US00PP36148P2

(12) United States Plant Patent
Smit

(10) Patent No.: US PP36,148 P2
(45) Date of Patent: Sep. 24, 2024

(54) ***BEGONIA* PLANT NAMED 'EC-BEGO-2304'**

(50) Latin Name: *Begonia maculata*
Varietal Denomination: EC-BEGO-2304

(71) Applicant: Eden Collection, BV, Sappemeer (NL)

(72) Inventor: Obed Jacob Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 18/387,372

(22) Filed: Nov. 6, 2023

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./343

CPC ... A01H 5/12; A01H 5/00; A01H 5/02; A01H 6/185; A01H 6/18
See application file for complete search history.

(56) References Cited

PUBLICATIONS

Mazo et al. Two new species of *Begonia* (section Petermannia, Begoniaceae) from Zamboanga Penisula, Philippines with notes on an amended description of B. elatostematoides, Taiwania 67(3): 441-449, 2022. (Year: 2022).*

* cited by examiner

*Primary Examiner* — June Hwu
(74) *Attorney, Agent, or Firm* — Cassandra Bright

(57) ABSTRACT

A new and distinct cultivar of *Begonia* plant named 'EC-BEGO-2304' is disclosed, characterized by curved, toothed, dark green leaves with silvery-white dots. Plants have strong stems with thick and glossy foliage. The new variety is a *Begonia*, typically used as an ornamental plant.

3 Drawing Sheets

Latin name of the genus and species: *Begonia maculata*.
Variety denomination: 'EC-BEGO-2304'.

BACKGROUND OF THE INVENTION

The new cultivar is a product of a planned breeding program to produce distinct and better performing *Begonia* varieties. The new variety was selected as a seedling resulting from the crossing made by the inventor, Obed J. Smit, a citizen of the Netherlands, in 2018. The seed parent is the unpatented *Begonia maculata* '180027', a variety from the inventor's breeding line. The pollen parent is an unnamed, unpatented specimen of *Begonia maculata*. The new variety was selected by the inventor in 2018 at a commercial greenhouse in Sappemeer, the Netherlands.

Asexual reproduction of the new cultivar 'EC-BEGO-2304' by terminal cuttings was first performed in Sappemeer, the Netherlands at a commercial greenhouse in March 2020, and has shown that the unique features of this cultivar are stable and reproduced true to type through successive generations.

SUMMARY OF THE INVENTION

The cultivar 'EC-BEGO-2304' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-BEGO-2304'. These characteristics in combination distinguish 'EC-BEGO-2304' as a new and distinct *Begonia* cultivar:

1. Very dark green leaf color with many small silvery-white dots.
2. Unique curved and toothed leaf-rim.
3. Strong stems.
4. Thick, glossy leaves.

PARENT COMPARISONS

Plants of the new cultivar 'EC-BEGO-2304' are similar to plants of the female parent in most horticultural characteristics, however, plants of the new cultivar 'EC-BEGO-2304' differ from in the following characteristics:

1. Leaf color of the new variety is dark green, while leaf color of the seed parent is dark red.
2. Leaves of the new variety are larger than leaves of the seed parent.
3. Plants of the new variety are larger than plants of the seed parent.

Plants of the new cultivar 'EC-BEGO-2304' are similar to plants of the male parent in most horticultural characteristics, however, plants of the new cultivar 'EC-BEGO-2304' differ in the following characteristics:

1. Leaf color of the new variety is dark green with silvery-white dots, while leaf color of the pollen parent is bright green with fewer white dots.
2. Leaf underside of the new variety is colored dark red, while leaf underside of the pollen parent is colored a lighter red.
3. Leaves of the new variety are bent slightly downwards, while leaves of the pollen parent grow horizontally.
4. Leaf venation of the new variety is clearly visible, while leaf venation of the pollen parent is hardly visible.

COMMERCIAL COMPARISONS

Plants of the new cultivar 'EC-BEGO-2304' are similar to plants of the commercial variety *Begonia* 'Double Dot', unpatented. However, plants of the new cultivar differ in the following characteristics:

1. Leaf color of the new variety is dark green with silvery-white dots, while the leaf color of this comparator is lighter green with white dots.
2. Leaf underside of the new variety is colored dark red, while leaf underside of this comparator is green.
3. Leaves of the new variety are curved with a deep-toothed rim, while leaves of this comparator are hardly curved with a shallow-toothed rim.

Plants of the new cultivar 'EC-BEGO-2304' are similar to plants of co-pending U.S. Plant patent application Ser. No. 18/387,381, 'EC-BEGO-2305'. However, plants of the new cultivar differ in the following characteristics:

1. Leaf color of the new variety is very dark green with silvery-white dots, while the leaf color of this comparator is dark green with fewer green-white dots.
2. Leaf underside of the new variety is colored dark red, while leaf underside of this comparator is green-red.
3. Leaves of the new variety are curved with a deep-toothed rim, while leaves of this comparator are hardly curved with a shallow-toothed rim.
4. Leaves of the new variety are smaller than leaves of this comparator.
5. Leaves of the new variety are glossy, while leaves of this comparator are not.

BRIEF DESCRIPTION OF THE PHOTOGRAPHS

The accompanying photograph in FIG. 1 illustrates in full color a typical plant of 'EC-BEGO-2304' grown in a greenhouse. The plant is approximately 30 weeks of age.

Figure 1:
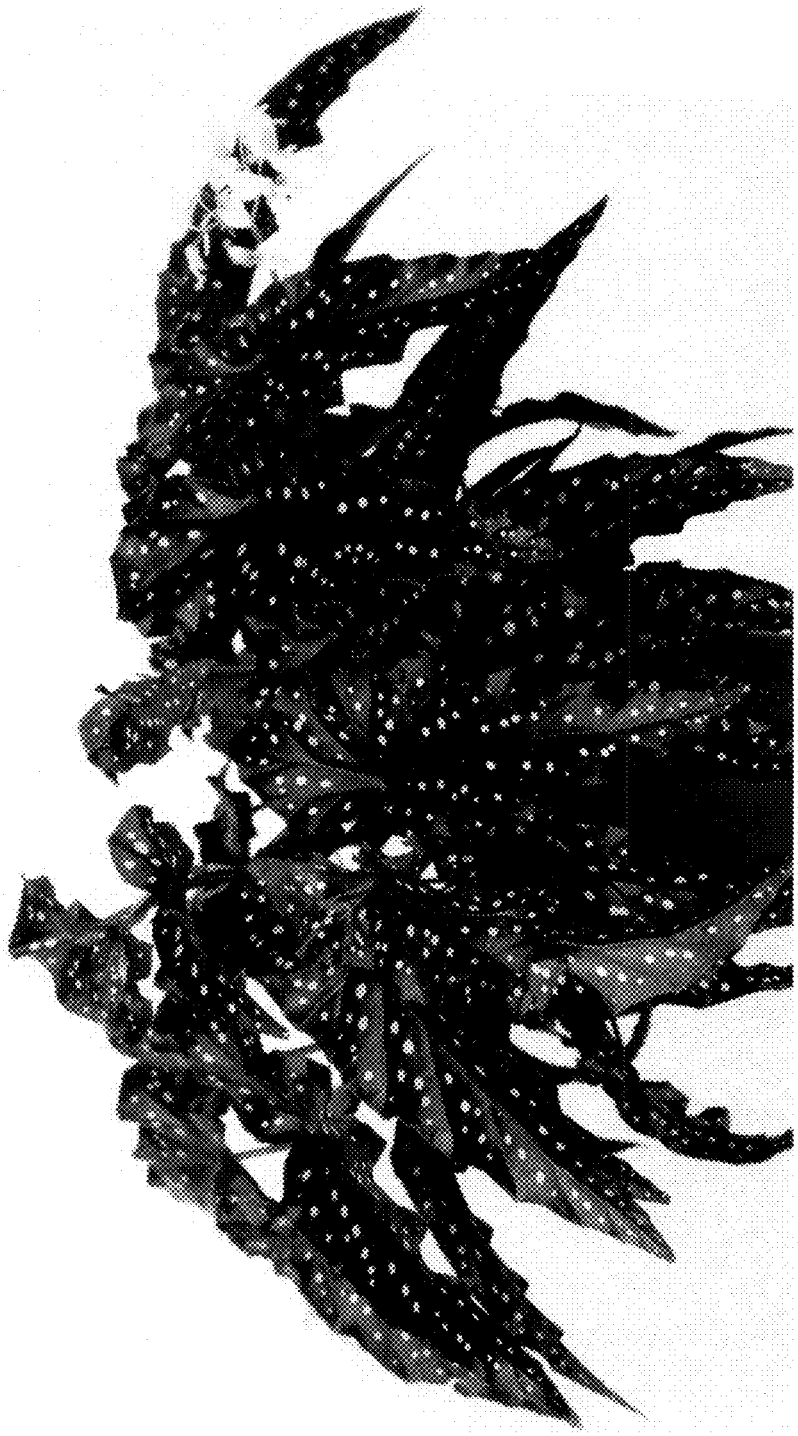
Figure 2:
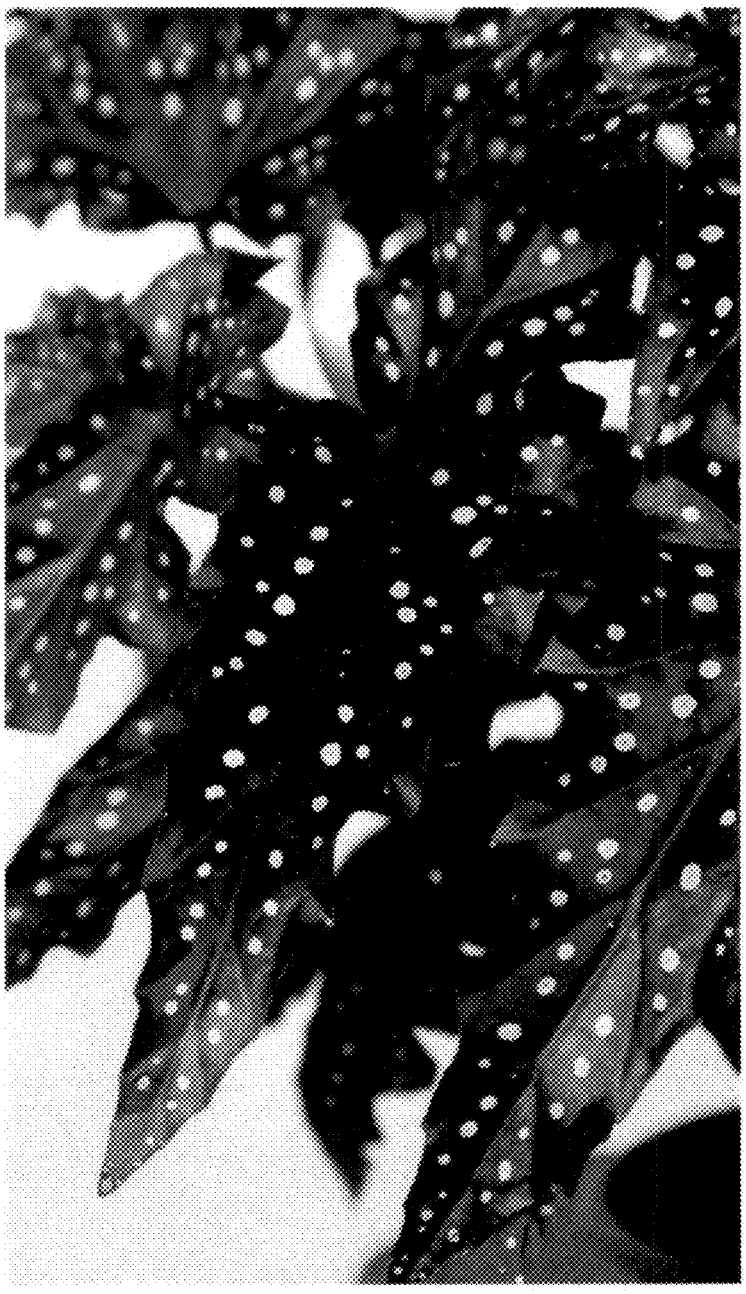
FIG. 2 illustrates a close up of the foliage.
Figure 3:
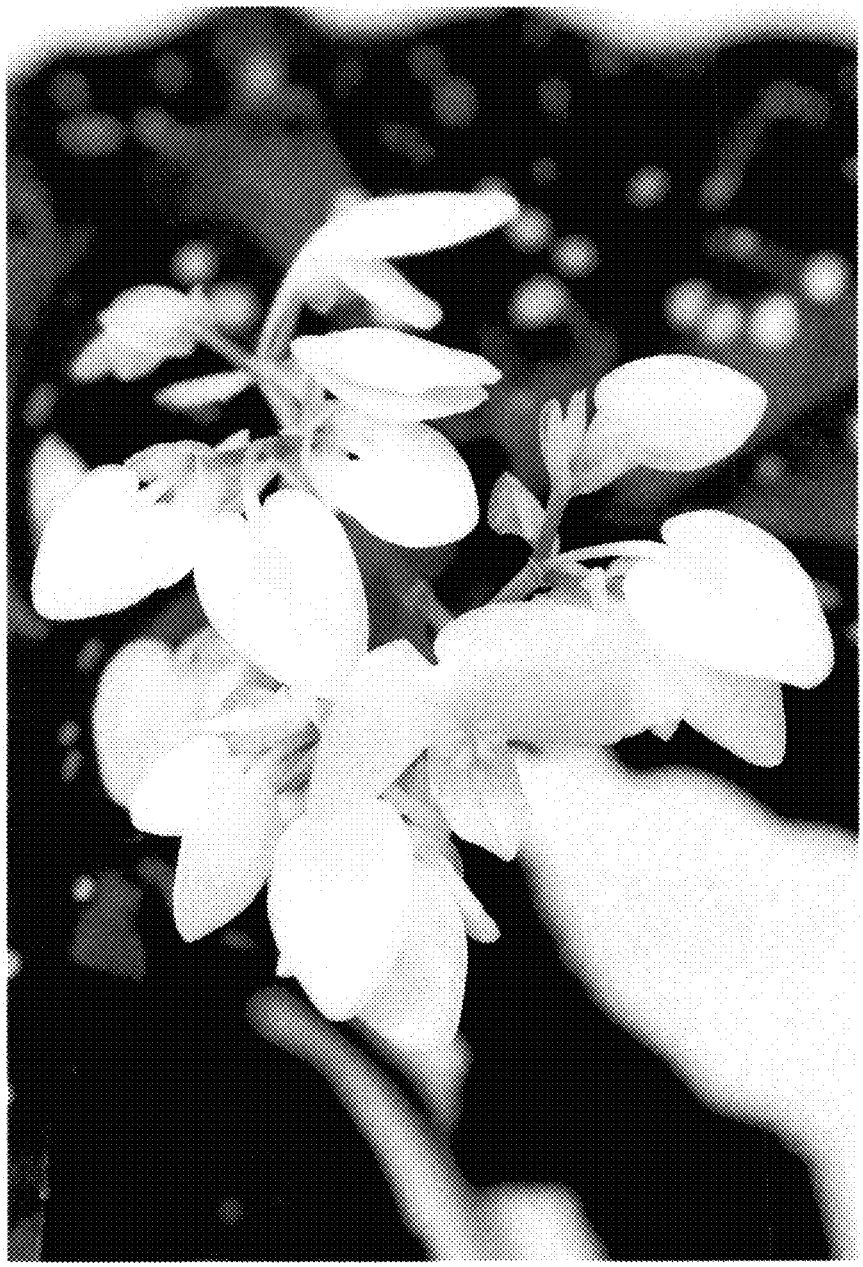
FIG. 3 illustrates flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-BEGO-2304' plants at 14 weeks of age, grown in a greenhouse in Sappemeer, the Netherlands during October. The growing temperature ranged from 16° C. to 20° C. at night to 18° C. to 20° C. during the day. Measurements and numerical values represent averages of typical flowering types.

Botanical classification: *Begonia maculata* 'EC-BEGO-2304'.

PROPAGATION

Time to initiate roots: About 21 days at approximately 21° C. in summer.

Time to produce rooted cutting: About 28 days at 21° C. in summer.

Description of roots: Fibrous, fine, moderately dense, freely branching. White in color, not accurately measured with RHS chart.

PLANT

Plant type: Perennial potted plant.

Plant shape: Flattened.

Growth habit: Very broad spreading and semi-upright.

Plant spread: Average 49.8 cm.

Height: Average 22.8 cm to top of foliar plane; 17.8 cm to top of floral plane.

Growth rate: Moderate.

Plant vigor: Moderate.

Age of plant described: Approximately 14 weeks from placing unrooted cuttings in the pots.

Branching habit: Moderately free branching, basal branches and few lateral branches.

Pinching: Pinching not required.

Number of primary (main) branches per plant: Average 7.

Number of secondary (lateral) branches per plant: Average 4.

Main branches:

*Length.*—Average 17.3 cm.

*Diameter.*—Average 0.55 cm.

Internode length: Average 3.2 cm.

Appearance and shape: Smooth, glabrous.

Luster: Moderately glossy.

Aspect: Average 30°.

Strength: Moderately weak.

Color:

*Developing.*—RHS Yellow-Green 146C.

*Mature.*—RHS Yellow-Green 146A.

*At internodes.*—RHS Greyed-Yellow 161C and 164D.

Pubescence: None.

Lenticels:

*Length.*—0.1 cm.

*Width.*—0.3 mm.

*Shape.*—Linear.

*Color.*—RHS Green-White 155C.

Other: Stems slightly zigzag, typical for many *Begonia* varieties.

FOLIAGE

Leaf:

*Arrangement.*—Alternate, single.

*Quantity.*—Average 12.

*Average length.*—19.5 cm.

*Average width.*—6.8 cm.

*Shape of blade.*—Obliquely lanceolate.

*Apex.*—Narrow acute.

*Base.*—Oblique, lobes touching.

*Margin.*—Toothed, undulate.

*Texture of top surface.*—Glabrous, smooth, slightly leathery.

*Texture of bottom surface.*—Glabrous, smooth, slightly leathery.

*Pubescence.*—None.

*Luster, upper side.*—Glossy.

*Luster, under side.*—Glossy.

*Rugosity, upper side.*—Non-rugose.

*Rugosity, under side.*—Non-rugose.

*Color.*—Young foliage upper side: RHS Grey-Brown N199A, tinged Yellow-Green 152A, moderately dotted with circular dots, average diameter: 0.25 cm, dots near the leaf margins smaller, average diameter: 0.1 cm, all dots colored Greyed-White 156D to Greyed-Green 190D, with a strong silvery-velvety shine. Quantity of dots moderate. Young foliage under side: RHS Greyed-Red 178A, lamina moderately dotted with circular dots, average diameter: 0.25 cm, dots near the leaf margins smaller, average diameter: 0.1 cm, all dots colored Greyed-Red 179A. Quantity of dots moderate. Mature foliage upper side: RHS Greyed-Green N189A, and tinged Black 203A, moderately dotted with broad elliptic dots, average length: 0.5 cm, average width: 0.35 cm, dots near the leaf margins smaller average length: 0.25 cm, average width: 0.2 cm, all dots colored White N155A, with a strong silvery-velvety shine. Quantity of dots moderate. Mature foliage under side: RHS Greyed-Purple, a blend of 183A and 187A.

*Venation.*—Pattern: Palmate-pinnate. Venation color upper side: RHS Yellow-Green 146A and 147A. Venation color under side: RHS Greyed-Purple 183B.

*Petiole.*—Average Length: 4.4 cm. Diameter: 0.35 cm. Texture: Glabrous, smooth. Luster: Moderately glossy. Strength: Low to moderate. Color, upper side: RHS Yellow-Green 146A, fading to 148A at the base. Color, under side: RHS Yellow-Green, a blend of 146A and 148A, proximal end tinged Greyed-Red 178A, distal end tinged Greyed-Purple 183A to 183B.

*Stipules.*—Quantity: 2 leafy stipules present at each node. Shape: Ovate. Average Length: 3.4 cm. Average width: 1.8 cm. Apex: Abruptly acute. Base: Broad cuneate. Margin: Entire. Color: Both sides colored RHS Yellow-Green 145B, thinly veined Grey-Brown 199D.

FLOWER

Inflorescence:
- *Type and form.*—Cyme.
- *Height.*—Average: 10.1 cm (including peduncle).
- *Diameter.*—Average: 6.1 cm.
- *Quantity of flowers per inflorescence.*—Average 27.
- *Quantity of inflorescences per plant.*—Average 5.
- *Quantity of flowers and buds per plant.*—Average 80.
- *Natural flowering season.*—Summer to autumn.

Flower bud:
- *Length.*—1.4 cm.
- *Diameter.*—Bud flattened, average width at widest: 1.1 cm, at narrowest: 0.3 cm.
- *Shape.*—Cordate, flattened.
- *Texture.*—Glabrous, velvety.
- *Luster.*—Matte.
- *Color.*—RHS White NN155B, center Yellow 11D.

Flower:
- *Type and form.*—Male flowers only, rotate, single.
- *Aspect.*—Outward to slightly drooping.
- *Flowering habit.*—Freely.
- *Fragrance.*—None.
- *Shape.*—Cruciform, single.
- *Height.*—Average: 2.6 cm.
- *Diameter.*—Average: 2.9 cm.
- *Length.*—Average: 1.2 cm.
- *Longevity on plant.*—Average 10 days.
- *Persistence.*—Self-cleaning.

Tepals:
- *Arrangement.*—Cruciform.
- *Quantity per flower.*—Average 4.
- *Number of whorls.*—Average 2.
- *Shape.*—Outer: Cordate to ovate. Inner: Oblong.
- *Length.*—Outer: Average 1.8 cm. Inner: Average 1.1 cm.
- *Width.*—Outer: Average 1.5 cm. Inner: Average 0.7 cm.
- *Apex.*—Outer: Acute. Inner: Abruptly acute.
- *Base.*—Outer: Cordate to truncate. Inner: Acute.
- *Margin.*—Entire, no undulation.
- *Texture.*—Outer: Glabrous, velvety all surfaces. Inner: Glabrous, moderately velvety all surfaces.
- *Rugosity.*—Non-rugose.
- *Luster.*—Matte.
- *Color inner and outer tepal.*—When opening: RHS White N155D. Fully opened: RHS White N155D. No visible venation.

Peduncle:
- *Terminal length.*—Average 8.2 cm.
- *Terminal diameter.*—Average 0.2 cm.
- *Secondary length.*—Average 5.1 cm.
- *Secondary diameter.*—Average 0.2 cm.
- *Angle to lateral branch axis.*—Average 5°.
- *Strength.*—Moderately weak.
- *Texture.*—Glabrous, smooth.
- *Luster.*—Moderately glossy.
- *Color.*—RHS Yellow-Green 152D, secondary peduncle strongly tinged Greyed-Red 181B.

Pedicel:
- *Length.*—Average 1.8 cm.
- *Diameter.*—Average 0.1 cm.
- *Angle to lateral branch axis.*—Primary flower straight on top of peduncle, secondary flowers in an average angle of 35° to peduncle.
- *Strength.*—Moderately weak.
- *Texture.*—Glabrous, smooth, moderately velvety.
- *Luster.*—Slightly glossy, moderately velvety.
- *Color.*—Transparent white; RHS White N155A.

Bracts: One pair of bracts is present below each individual flower.
- *Shape.*—Broad ovate.
- *Apex.*—Acute.
- *Margin.*—Entire.
- *Base.*—Broad cuneate.
- *Length.*—Average 0.7 cm.
- *Width.*—Average 0.6 cm.
- *Texture.*—Both sides smooth, glabrous, slightly glossy and slightly velvety.
- *Color.*—Transparent white; RHS White N155A.

REPRODUCTIVE ORGANS

Stamens:
- *Number.*—Average 35.
- *Filament length.*—Average 0.2 cm.
- *Filament color.*—RHS Yellow 4C.

Anther:
- *Shape.*—Obovate.
- *Length.*—Average 0.1 cm.
- *Width.*—Average 0.75 cm.
- *Color.*—RHS Yellow 4A.
- *Pollen.*—Low.
- *Pollen color.*—RHS Yellow 11A.

No gynoecium present.

OTHER CHARACTERISTICS

Seeds and fruits: None observed to date.

Disease/pest resistance: Similar resistance nor susceptibility to normal diseases and pests of *Begonia* has been observed.

Temperature tolerance: Tolerates temperatures up to 35° C. Hardy to USDA zones 10 to 12. Low to moderate tolerance to rain. Low tolerance to wind.

What is claimed is:

1. A new and distinct cultivar of *Begonia* plant named 'EC-BEGO-2304' as herein illustrated and described.

* * * * *